United States Patent [19]

Kattan

[11] Patent Number: 6,093,404
[45] Date of Patent: Jul. 25, 2000

[54] THERAPEUTIC COMPOSITION

[76] Inventor: Maha Kattan, 620 Live Oak Dr., McLean, Va. 22101

[21] Appl. No.: 09/342,247

[22] Filed: Jun. 29, 1999

[51] Int. Cl.[7] .................................................. A61K 35/78
[52] U.S. Cl. ......................................................... 424/195.1
[58] Field of Search ........................................... 424/195.1

[56] References Cited

U.S. PATENT DOCUMENTS

| | | |
|---|---|---|
| 4,258,055 | 3/1981 | Lietti et al. . |
| 4,489,067 | 12/1984 | Uenobe et al. . |
| 4,698,360 | 10/1987 | Masquelier . |
| 5,607,965 | 3/1997 | Kondo et al. . |
| 5,719,178 | 2/1998 | Paul et al. . |
| 5,804,168 | 9/1998 | Murad . |

FOREIGN PATENT DOCUMENTS

| | | |
|---|---|---|
| 2013443 | 5/1994 | Russian Federation . |
| 9200844 | 9/1993 | Sweden . |

OTHER PUBLICATIONS

Han, CAPLUS Abstract of Taehan Yakrihak Chapchi, vol. 8, No. 1, pp. 27–30, 1972.

Krecman et al. Planta Medica, vol. 64, No. 2, pp. 138–142, Mar. 1998.

*Primary Examiner*—Francisco Prats
*Assistant Examiner*—Susan D. Coe
*Attorney, Agent, or Firm*—Larson & Taylor, PLC

[57] ABSTRACT

A therapeutic composition and a method of use therefor in adults and children are disclosed. The therapeutic composition alleviates symptoms associated with attention deficit disorder (ADD) and attention deficit hyperactivity disorder (ADHD) including hyperactivity, impulsivity, and inattentiveness. The therapeutic composition contains proanthocyanidin, yucca root, hawthorn berry, bilberry, silymarin complex, and ginkgo biloba. The therapeutic composition is taken in a single daily dose.

1 Claim, No Drawings

THERAPEUTIC COMPOSITION

FIELD OF THE INVENTION

The present invention relates to therapeutic compositions for treating attention deficit disorder (ADD) and attention deficit hyperactivity disorder (ADHD) in children and adults, and more particularly to a single dose therapeutic composition comprising all-natural herbs and antioxidants.

BACKGROUND OF THE INVENTION

Attention Deficit Disorder (ADD) and Attention Deficit Hyperactivity Disorder (ADHD) are among the most common mental disorders among children. ADHD also often continues into adolescence and adulthood.

ADD and ADHD are diagnoses applied to children and adults who consistently display certain characteristic behaviors over a period of time. The most common behaviors include inattention, hyperactivity, and impulsivity.

Inattentive behavior is often characterized by difficulty focusing on one task and persisting until completion, a failure to pay attention to details, and making careless mistakes in a variety of tasks. Individuals exhibiting inattentive behavior may appear as if their minds are elsewhere or they are not listening or did not hear what has just been said.

Hyperactive people always seem to be in motion and may suffer from feelings of restlessness and difficulty engaging in sedentary activities. Common signs of hyperactivity include excessive unproductive movement, such as fidgeting with hands or feet, excessive talking, and an inability to sit still. Hyperactive children often squirm in their seats, roam around the room, and feel compelled to touch everything.

Impatience and a failure to think before acting often characterize impulsivity. Impulsive young children may frequently interrupt others, fail to listen to directions, and have difficulty waiting their turn.

Scientists have not yet identified a single underlying cause behind these behavior characteristics. While some have been linked to decreased brain activity, the biological reason for the decreased brain activity is still unknown. Treatment for ADD and ADHD is therefore limited to treating the symptoms of the disorders.

The most common treatment for ADD and ADHD is the use of mild central nervous system stimulant drugs, such as Ritalin, Cylert, and Dexedrine. However, there are several drawbacks to using these drugs. Frequent short-term side effects include loss of appetite, insomnia, headaches, stomachaches, drowsiness, hyperactivity, blood pressure and pulse changes, and cardiac arrhythmia. In addition, little is known about the possible consequences of long-term exposure to these drugs in children. The use of Ritalin in children under six years of age is particularly undesirable since safety and efficacy in this age group has not been established.

As an alternative to the aforementioned conventional treatments, U.S. Pat. No. 5,719,178 discloses a method of treating ADHD utilizing proanthocyanidin. The method comprises taking a quantity of proanthocyanidin sufficient to relieve symptoms of ADHD every approximately 3.5 to 4.0 hours. A heterocyclic antidepressant may be taken with the proanthocyanidin to relieve symptoms of "spaciness" or lack of cognitive focus. However, a major drawback of this method is that repeated doses are required to alleviate symptoms throughout the day. Requiring repeated doses may be inconvenient as well as embarrassing, especially for school-aged children.

SUMMARY OF THE INVENTION

Thus, it is the purpose of the present invention to provide an all-natural therapeutic composition for treating symptoms associated with ADD and ADHD comprising proanthocyanidin, yucca, hawthorn, bilberry, silymarin complex, and ginkgo biloba. It is also a purpose of the present invention to provide a method of use for the therapeutic composition of the present invention.

DESCRIPTION OF THE PREFERRED EMBODIMENTS

The therapeutic composition of the present invention is an herbal remedy for alleviating symptoms of ADD and ADHD. The composition includes six natural herbs and antioxidants: proanthocyanidin, yucca schidigera, bilberry, hawthorn, silymarin complex, and ginkgo biloba. The inventor has discovered that these herbs and antioxidants work effectively together to alleviate symptoms of ADD and ADHD when administered on a daily basis. Proanthocyanidin is an extract from the bark of European coastal pine trees, commonly referred to by the trade name "Pycnogenol". It is a flavonoid and a powerful antioxidant, neutralizing free radicals in the body which result in strengthened blood vessels and improved circulation. Proanthocyanidin is water-soluble and easily absorbed by the body, making it more effective than many other commonly prescribed flavonoids. In addition, it is important for brain function, since it is one of the few dietary antioxidants that readily crosses the blood-brain barrier.

*Yucca schidigera* (Yucca) is a member of the lily family and the root is used for several therapeutic purposes. It is a useful treatment for chronic degenerative diseases and joint inflammation due to its ability to break up inorganic mineral obstructions and deposits. Yucca root extract also works to clean the colon and regulate colonic bacteria, reducing the burden on other eliminative systems of the body. Yucca is rich in vitamin A, B-complex, and vitamin C, and is a good source of calcium, copper, manganese, potassium and phosphorous.

Bilberry is a perennial ornamental shrub commonly found in a variety of climates. In the United States, bilberries are known as huckleberries. The bilberry fruit contains flavonoids and anthocyanin, a natural antioxidant. Bioflavonoids are also extremely efficient antioxidants and assist the body in countering the harmful effects of free radicals. Anthocyanin strengthens the body's small blood vessels, lowers blood pressure, reduces clotting, and improves circulation through larger blood vessels. Bilberry also contains gluoquinine that has the ability to lower blood sugar.

Bilberry has been shown to improve visual accuracy in healthy people and to help those with eye diseases such as pigmentosa, retinitis, glaucoma, and myopia. Bilberry has also been used as a treatment for diarrhea, nausea, and indigestion.

Hawthorn is obtained from the berries of the hawthorn tree. It is known to positively affect the cardiovascular system and is also used to treat digestive problems and insomnia. Hawthorn works as a vasodilator, increasing blood and oxygen flow to the heart and lowering blood pressure. By increasing the efficiency of the heart, hawthorn also increases blood flow to the rest of the body. Components in hawthorn have been shown to lower cholesterol and the amount of plaque in arteries.

Silymarin complex is found in the seeds of the Milk Thistle plant flower. It is most commonly used to protect and rejuvenate the liver. Silymarin exerts a membrane-stabilizing action preventing or inhibiting membrane peroxidation. Silymarin binds to liver cells, creating a shield against other liver-harming substances. In addition to shielding the liver, silymarin complex helps synthesize new proteins and ultimately regenerate damaged liver cells. Silymarin is used to halt or reverse liver damage from alcohol, pesticides, mushroom poisoning, and hepatitis. Silymarin also helps with the digestion of fats.

*Ginkgo Biloba* (Ginkgo) is obtained from the leaf of the ginkgo tree. Ginkgo works by increasing blood flow to the brain and blood vessels, resulting in higher oxygen levels in the brain. Benefits of enhanced circulation in the brain include improved short and long term memory, improved mental clarity, and increased energy levels.

It has been found that the therapeutic composition is useful in treating the symptoms of ADD and ADHD, without any adverse side effects. A single daily dose, taken in the morning effectively alleviates symptoms of ADD and ADHD throughout the entire day.

In a preferred embodiment of the invention, the therapeutic composition comprises the following herbs shown in percentages by weight of the total composition:

| Compound | % by Weight |
|---|---|
| Proanthocyanidin | 3–9 |
| Yucca Root | 30–40 |
| Hawthorn Berry | 15–25 |
| Bilberry | 10–20 |
| Silymarin Complex | 5–15 |
| Ginkgo Biloba | 10–15 |

The actual daily dosage of the composition is dependent upon the weight of the subject. In the preferred and most preferred embodiments of the invention, for the given weight ranges of the subject, the therapeutic composition comprises the following:

| Weight 30–50 lbs. | Preferred | Most Preferred |
|---|---|---|
| Proanthocyanidin | 13–39 mg | 20 mg |
| Yucca Root | 130.5–174 | 160 mg |
| Hawthorn Berry | 65–108.75 | 100 mg |
| Bilberry | 43.5–87 | 70 mg |
| Silymarin Complex | 21.75–65 | 30 mg |
| Ginkgo Biloba | 43.5–65 | 55 mg |
|  | 317.25–538.75 mg/day | 435 mg/day |

| Weight 50–90 lbs. | Preferred | Most Preferred |
|---|---|---|
| Proanthocyanidin | 16.65–50 mg | 40 mg |
| Yucca Root | 166.5–222 | 200 mg |
| Hawthorn Berry | 83–138.75 | 100 mg |
| Bilberry | 55.5–111 | 100 mg |
| Silymarin Complex | 27.75–83 | 40 mg |
| Ginkgo Biloba | 55.5–83 | 75 mg |
|  | 404.9–687.75 mg/day | 555 mg/day |

| Weight 90–150 lbs. | Preferred | Most Preferred |
|---|---|---|
| Proanthocyanidin | 33–100 mg | 80 mg |
| Yucca Root | 333–444 | 400 mg |
| Hawthorn Berry | 166.5–277.5 | 200 mg |
| Bilberry | 110–222 | 200 mg |
| Silymarin Complex | 55.5–166.5 | 80 mg |
| Ginkgo Biloba | 110–166.5 | 150 mg |
|  | 808–1,376.5 mg/day | 1110 mg/day |

| Weight 150–220 lbs. | Preferred | Most Preferred |
|---|---|---|
| Proanthocyanidin | 50–150 mg | 120 mg |
| Yucca Root | 500–666 | 600 mg |
| Hawthorn Berry | 249.75–416.25 | 300 mg |
| Bilberry | 166–333 | 300 mg |
| Silymarin Complex | 83.25–249.75 | 120 mg |
| Ginkgo Biloba | 166–249.75 | 225 mg |
|  | 1,215–2,064.75 mg/day | 1665 mg/day |

| Weight over 220 lbs. | Preferred | Most Preferred |
|---|---|---|
| Proanthocyanidin | 52.5–157.5 mg | 150 mg |
| Yucca Root | 500–666 | 600 mg |
| Hawthorn Berry | 249.75–416.25 | 300 mg |
| Bilberry | 166–333 | 300 mg |
| Silymarin Complex | 87.5–262.5 | 150 mg |
| Ginkgo Biloba | 175–262.5 | 250 mg |
|  | 1,230.75–2,097.75 mg/day | 1750 mg/day |

The invention is illustrated in the following examples wherein the composition was administered as a single daily dosage in the indicated quantities:

EXAMPLE 1

The therapeutic composition for the weight range 30–50 lbs. was administered to a four-year-old boy. The boy had been diagnosed with a learning disorder and exhibited symptoms of ADD and ADHD. Starting at about age 2, several therapies were tried prior to using the composition of the invention, including a restrictive diet with mega multi-vitamins for about nine months, with no success. Subsequently, high doses of magnesium and B6 were tried for approximately eight months, also with no improvement.

Another therapy of administering high doses of Pycnogenol alone for approximately six months also failed to relieve the symptoms. Within approximately six weeks of administering the therapeutic composition of the present invention, a dramatic improvement was seen. The boy's ability to remain seated, follow through on instructions, and play or work quietly was greatly improved. In addition, he was less fidgety and better able to focus on schoolwork. After taking the composition for almost five years, the results of a single missed dose are immediate. The boy becomes cranky, fidgety and emotionally unbalanced. The dosage was increased to that of the 50–90 lb. range when the boy's weight exceeded 50 lbs.

EXAMPLE 2

The therapeutic composition, for the weight range 90–120 lbs., was administered to a ten-year old boy diagnosed with ADHD. After approximately four weeks on the therapeutic composition, the symptoms of ADHD were significantly lessened.

EXAMPLE 3

The therapeutic composition, for the weight range 90–120 lbs. was administered to a ten-year old boy diagnosed with ADHD. Favorable results were seen after five weeks on the composition.

EXAMPLE 4

The therapeutic composition, for the weight range 90–120 lbs. was administered to an eleven-year old boy diagnosed with ADHD. Some positive effects were seen after ten days and within another week alleviation of the symptoms was consistent.

EXAMPLE 5

A thirteen-year old boy and a fourteen-year old boy, diagnosed with ADHD, were each given the therapeutic composition for the 90–120 lb. weight range. Both achieved favorable results within approximately five weeks.

EXAMPLE 6

The therapeutic composition for the weight range 90–120 lbs. was administered to a female adult diagnosed with ADHD. After approximately three weeks, an increase in concentration and greater ability to generate sequenced thoughts was noticed. In addition, she reported having much more focus and was able to follow through and complete tasks.

EXAMPLE 7

The therapeutic composition for the weight range 90–120 lbs. was administered to a female adult. Within 10 days, the woman reported favorable results including feeling calmer. After taking the composition for a month the woman reported feeling "normal."

EXAMPLE 8

The therapeutic composition, for weights 150 lbs. and over, was administered to an adult male diagnosed with ADHD. After approximately three weeks, he reported experiencing relief from the ADHD symptoms. He also reported being much more alert and generally functioning more efficiently in his everyday tasks.

EXAMPLE 9

The therapeutic composition, for weights 150 lbs. and over, was administered to an adult male diagnosed with ADHD. In less than two months, the man was performing better at work, and acting more responsibly and more focused. After achieving positive results, the man stopped taking the composition. Within three days of stopping the treatment, the man became irritable and forgetful.

Although the invention has been described in considerable detail with respect to preferred embodiments thereof, variations and modifications will be apparent to those skilled in the art without departing from the spirit and scope of the invention as set forth in the claims.

We claim:

1. A therapeutic composition for treatment of ADD or ADHD comprising in percentage by weight: 3–9% proanthocyanidin, 30–40% yucca root, 15–25% hawthorn berry, 10–20% bilberry, 5–15% silymarin, and 10–15% gingko biloba.

* * * * *